US011684570B2

(12) United States Patent
Liegner et al.

(10) Patent No.: US 11,684,570 B2
(45) Date of Patent: *Jun. 27, 2023

(54) PHARMACEUTICAL OPHTHALMIC COMPOSITIONS

(71) Applicants: NOVEL DRUG SOLUTIONS LLC, Randolph, NJ (US); EYE CARE NORTHWEST, PA, Sparta, NJ (US)

(72) Inventors: Jeffrey T. Liegner, Boise, ID (US); John Scott Karolchyk, Lake Hopatcong, NJ (US); Bernard Covalesky, Randolph, NJ (US); Richard Dilzer, Long Valley, NJ (US); Kalian Peters, Flemington, NJ (US)

(73) Assignees: NOVEL DRUG SOULTIONS LLC, Randolph, NJ (US); EYE CARE NORTHWEST, PA, Sparta, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/819,076

(22) Filed: Aug. 11, 2022

(65) Prior Publication Data

US 2022/0387308 A1 Dec. 8, 2022

Related U.S. Application Data

(60) Division of application No. 17/084,514, filed on Oct. 29, 2020, now Pat. No. 11,439,590, which is a division of application No. 15/178,812, filed on Jun. 10, 2016, now abandoned, which is a continuation-in-part of application No. 14/227,819, filed on Mar. 27, 2014, now abandoned.

(60) Provisional application No. 61/958,170, filed on Jul. 22, 2013.

(51) Int. Cl.
| A61K 9/48 | (2006.01) |
| A61K 31/196 | (2006.01) |
| A61K 31/573 | (2006.01) |
| A61K 31/58 | (2006.01) |
| A61K 45/06 | (2006.01) |
| A61K 47/10 | (2017.01) |
| A61K 47/22 | (2006.01) |
| A61K 47/38 | (2006.01) |
| A61K 9/00 | (2006.01) |
| A61K 31/4709 | (2006.01) |
| A61K 38/14 | (2006.01) |
| A61K 31/496 | (2006.01) |
| A61K 38/12 | (2006.01) |

(52) U.S. Cl.
CPC .......... *A61K 9/0048* (2013.01); *A61K 31/196* (2013.01); *A61K 31/4709* (2013.01); *A61K 31/496* (2013.01); *A61K 31/573* (2013.01); *A61K 31/58* (2013.01); *A61K 38/12* (2013.01); *A61K 38/14* (2013.01); *A61K 45/06* (2013.01); *A61K 47/10* (2013.01); *A61K 47/22* (2013.01); *A61K 47/38* (2013.01)

(58) Field of Classification Search
CPC ...................................................... A61K 9/48
See application file for complete search history.

(56) References Cited

U.S. PATENT DOCUMENTS

| 3,138,528 | A | 6/1964 | Marcus et al. |
| 5,149,694 | A | 9/1992 | Cagle |
| 5,227,165 | A | 7/1993 | Domb |
| 5,459,157 | A | 10/1995 | Stroppolo et al. |
| 5,461,081 | A | 10/1995 | Ali et al. |
| 5,525,349 | A | 6/1996 | Robertson |
| 5,540,930 | A | 7/1996 | Guy |
| 5,611,464 | A | 3/1997 | Tsao |
| 5,803,966 | A | 9/1998 | Kulshreshtha |
| 6,037,328 | A | 3/2000 | Hu |
| 6,166,012 | A | 12/2000 | Muller |
| 6,359,016 | B2 | 3/2002 | Singh et al. |
| 6,372,814 | B1 | 4/2002 | Sun |
| 6,716,830 | B2 | 4/2004 | Cagle et al. |
| 7,563,256 | B2 | 7/2009 | Hearne |
| 7,842,714 | B2 | 11/2010 | Farnes |
| 8,541,413 | B2 | 9/2013 | Wong |
| 8,993,636 | B2 | 3/2015 | Cagle et al. |
| 9,403,941 | B2 | 8/2016 | Emanuele et al. |
| 2001/0049366 | A1 | 12/2001 | Singh et al. |
| 2002/0028816 | A1 | 3/2002 | Cagle et al. |

(Continued)

FOREIGN PATENT DOCUMENTS

| CN | 101015558 A | 8/2007 |
| EP | 1384478 | 1/2004 |

(Continued)

OTHER PUBLICATIONS

Angelucci, Diane, Interacameral injection studied to replace post-op eyedrops, Jan. 2006 Online [retrived from the internet on Aug. 18, 2015] URL:http://www.eyeworld.org/article.php?SID=2918.

(Continued)

*Primary Examiner* — Sarah Alawadi
(74) *Attorney, Agent, or Firm* — Browdy and Neimark, PLLC

(57) ABSTRACT

Pharmaceutical ophthalmic compositions are described, the compositions consisting essentially of a therapeutically effective quantity of an anti-bacterial agent (such as moxifloxacin), a therapeutically effective quantity of an anti-inflammatory agent (such as prednisolone), a combination of at least two solubilizing and suspending agents (of which one is a non-ionic polyoxyethlene-polyoxypropylene block copolymer), and a carrier. Methods for fabricating the compositions and using them are also described.

4 Claims, No Drawings

(56) References Cited

U.S. PATENT DOCUMENTS

| | | |
|---|---|---|
| 2002/0193370 A1 | 12/2002 | Cagle |
| 2004/0141925 A1 | 7/2004 | Bosch et al. |
| 2004/0198829 A1 | 10/2004 | Sponsel et al. |
| 2005/0085446 A1 | 4/2005 | Babu et al. |
| 2006/0166879 A1 | 7/2006 | Bhushan et al. |
| 2006/0172972 A1 | 8/2006 | Bhushan et al. |
| 2006/0205682 A1 | 9/2006 | Roberls et al. |
| 2006/0276777 A1 | 12/2006 | Coroneo |
| 2007/0049552 A1 | 3/2007 | Babu et al. |
| 2007/0077209 A1 | 4/2007 | Baran |
| 2007/0148192 A1 | 6/2007 | Laddha et al. |
| 2007/0196350 A1 | 8/2007 | Bartels |
| 2008/0262415 A1 | 10/2008 | Peyman |
| 2010/0239637 A1 | 9/2010 | Ciolino et al. |
| 2011/0082125 A1 | 4/2011 | Singh et al. |
| 2011/0230963 A1 | 9/2011 | Cuevas |
| 2012/0070401 A1 | 3/2012 | Zhang et al. |
| 2012/0082627 A1 | 4/2012 | Yelin et al. |
| 2012/0277199 A1 | 11/2012 | Ye et al. |
| 2012/0321719 A1 | 12/2012 | McDonnell et al. |
| 2013/0065888 A1 | 3/2013 | Biserka |
| 2013/0178801 A1 | 7/2013 | Branch et al. |
| 2014/0127269 A1 | 5/2014 | Masli |
| 2015/0024996 A1 | 1/2015 | Liegner et al. |
| 2015/0025511 A1 | 1/2015 | Wiley |
| 2015/0037422 A1 | 2/2015 | Kaplan et al. |
| 2015/0129457 A1 | 5/2015 | Flodin et al. |
| 2015/0164882 A1 | 6/2015 | Dilzer |
| 2016/0101118 A1 | 4/2016 | Fernandez et al. |
| 2016/0175323 A1 | 6/2016 | Wiley |
| 2016/0184323 A1 | 6/2016 | Wiley et al. |
| 2016/0243031 A1 | 8/2016 | Wiley et al. |
| 2016/0279055 A1 | 9/2016 | Liegner et al. |

FOREIGN PATENT DOCUMENTS

| | | |
|---|---|---|
| EP | 1688144 | 9/2006 |
| EP | 2462921 | 6/2012 |
| JP | 2002522373 A | 7/2002 |
| JP | 2008-540532 | 11/2008 |
| JP | 2008540532 A | 4/2011 |
| JP | 2013-508381 A | 3/2013 |
| WO | 1990001933 | 3/1990 |
| WO | 2000007565 A2 | 2/2000 |
| WO | 2006/121963 A2 | 11/2006 |
| WO | 2006121963 A2 | 11/2006 |
| WO | 2007011874 | 1/2007 |
| WO | 2008144347 A1 | 11/2008 |
| WO | 2011/049958 A2 | 4/2011 |
| WO | 2011/049960 | 4/2011 |
| WO | 2011/050206 | 4/2011 |
| WO | 2011049958 A2 | 4/2011 |
| WO | 2011/106702 | 9/2011 |
| WO | 2011157428 | 12/2011 |
| WO | 2012/062834 | 5/2012 |
| WO | 2013/065028 | 5/2013 |
| WO | 2013/065029 | 5/2013 |
| WO | 2013126799 | 8/2013 |
| WO | 2015/012899 | 1/2015 |

OTHER PUBLICATIONS

Liegner et al. Transzonular Intravitreal Injection of Triamcinolone and Moxifloxicin After IOL Insertion in Lieu of Preop/Postop Eyedrops., Apr. 24, 2012 Online [retrieved from internet on Aug. 18, 2015] URL:http://ascrs2012.conferencefilms.com/atables.wcs?entryid=00047.

Mangan et al., No endophthalmitis seen in case series of 'no drop' catacract surgery, Primary Care Optometry News Jul. 2013, 18(7):16.

Pagnelli et al., A single intraoperative sub-tenon's capsule injection of triaminolene and ciprofloxacin in a controlled-release system for cataract surgery, Investigative Opthamology & Visual Science, Jul. 2009, 50(7):3041-3047.

Ermis et al., Treatment of Staphylococcus epidermidis endopthalmitis with intravitreal moxifloxacin in a rabbit model., Tohoku Journal of Experimental Medicine, Mar. 2005, 205(3):233-229.

Sakalar el al., Treatment of experimental Bacillus cereus endophthalmitis using intravitreal moxifloxacin with or without dexamethasone, Journal of Ocular Pharmacology and Therapeutics: The Official J of the Assoc for Ocular Pharmacology and Therapeutics, Dec. 2011, 27(6):593-598.

Wiskur et al., Toward improving therapeutic reimens for Bacillus endopthalmitis, Investigative Ophthalmology & Visual Science, Apr. 2008, 49(4):11480-1487.

Kumar et al., Trans-zonular delivery of intravitreal triamcinolone acetonide in the management of pre-existing mascular oedema during cataract surgery, ACTA Ophthalmologica Scandinavica, Jun. 2006, 84(3):438-440.

Mangan, Richard, Transzonular injection reduces need for post operative eye drops, Nebraska Optometric Association Aug. 13, 2013, Online [retrieved from internet on Aug. 19, 2015] URL:http://nebraska.aoa.org/Documents/NE/FallConvention/OD/LenticularCOMNGTRIMOX2013BW.pdf.

PCT/US2014/032026 International Search Report dated Jul. 31, 2014.

Bertino, Jr., Impact of Antiboiotic Resistance in the Management of Ocular Infections: the role of current and future antibiotics, Clin. Opthalmol., Sep. 24, 2009, 3:507-21.

Hook's Apothecary:: Log of Scripts—Prescriptions filled between Jun. 18, 2011 and Jun. 18, 2015 (Triamcinolone/Floxacin 15mg/1mg Injectable), The Compounder RX-PCCA-Server(4.10.8.5), Printed Jun. 18, 2015.

Helzner, Jerry, A case for dropless cataract surgery, Opthalmology Management, May 2014, 18:46, 48, 50, 51, 53, 71.

Liegner, Jeffrey T., Innovations in Ophthalmology: Dropless Cataract Surgery, Cataract & Refractive Surgery Today, Jan. 2015, 70-71.

Imprimis Pharmaceuticals, Inc., Imprimis Pharmaceuticals Reports on Positive Clinical Findings Presented at the American Academy of Ophthalmology (AAO) Annual Meeting, PR Newswire, Oct. 24, 2014.

Liegner, Jeffrey, Subject: an unfulfiled interest in the patented Imprimis product TriMoxiVanc in your Indiana ASC, E-mail transmitted Feb. 6, 2015.

Kassem et al., Nanosuspension as an opthalmic delivery system for cetain glucocorticoid drugs, International Journal of Pharmaceutics, 2007, 340:126-133, Elsevier.

PCTIUS2017/030//2 Inlernational Search Reporl and Written Opinion dated Aug. 10, 2017.

Huerva et al., Levels of Vancomycin in Aqueous Humor After Topical Eye Drops Administration, Journal of Ocular Pharmacology, 1993, 9(2):167-170.

JP2016-529754 Office Action dated Oct. 24, 2017.

John, Biju, Intravitreal Injections, Kerala Journal of Ophthalmology, Mar. 2007, col. XIX, No. 1, pp. 46-57.

Gallemore, Ron P., NSAIDs in Treatment of Retinal Disorders, Review of Opthalmology, Nov. 15, 2006, 16 pages.

Campos et al., Efficacy and tolerability of a fixed-dose oxifloxacin-dexamethasone formulation for topical prophylaxis in LASIK: a comparative, double-masked clinical trial, Clin Ohthalmol., 2008, 2(2):331-338, Dovepress.

Kurz et al., Injectable Intraocular Corticosteroids, Surgical Manageent of Inflamatory Eye Disease, 2008, Becker and Davis, Eds., Chapter 1, Spinger.

Lipner, Maxine, "Perioperative pharmacology. Bucking the drop trend." May 2012 Online [retrieved from internet on Aug. 18, 2015] URL: http://eyeworid.org/article-bucking-lhe-drop-trend.

Deresinski (Vancomycin in Combination with Other Antibiotics for the Treatment of Serious Methicillin Staphylococcus aureus Infections) (Year: 2009).

Sigma. Pluronic F-68 (Year: 2015).

Sigma. Triamicinolone (Year: 2019).

Huerva et al., Levels of Vancomycin in Aqueous Humor After Topical Eye Drops Adminstration (1993).

(56) References Cited

OTHER PUBLICATIONS

Wittpenn et a l. A Randomized Masked Comparison of Topical Ketorolac 0.4% Plus Steroid vs Steroid Alne in Low-Risk Cataract Surgery Patients 2008.

Lobo., Conceicao, Pseudophakic Cystoid Macular Edema. Ophthalmologica, Jul. 28, 2011, 227:61-67.

Heier. Ketorolac Versus Prednisolone Versus Combination Therapy In the Treatment of Acute Pseudophakic Cystoid Macular Edema, Ophthalmology, Nov. 2000, 107(11):2034-2038, Elsevier Science Inc.

Couch et al. (Intravitreal triamcinolone for intraocular inflammation and associated macular edema (Year 2009).

Devi et al., Poloxamer: A Novel Functional Molecule For Drug Delivery And Gene Therapy, J. Pharm. Sci. & Res., 5(8):159-165 (2013).

Domb et al., Handbook of Biodegradable Polymers, pp. 232-233(1997).

Kabanov et al., Pluronic® block copolymers: novel functional molecules for gene therapy, Advanced Drug Delivery Reviews, 54:223-233 (2002).

Kolliphor P 188 Bio, Poloxamer Ph. Eur., Poloxamer USP/NF, Polyoxyethylene (160) Polyoxypropylene (30) Glycol JPE Poloxamer for Pharmaceutical Use, pp. 1-7 (2021).

Patel et al., Poloxamers: A pharmaceutical excipients with therapeutic behaviors, International Journal of PharmTech Research, 1(2):299-303 (2009).

Pitto-Barry et al., Pluronic® block-copolymers in medicine: from chemical and biological versatility to rationalisatior and clinical advances, Polym. Chem, 5:3291-3297 (2014).

Schmolka, Polymers for Controlled Drug Delivery, Poloxamers in the Pharmaceutical Industry, Chapter 10 pp. 189-192 (1991).

Singhare et al., Poloxamers: Promising Block Co-Polymers in Drug Delivery, Indian J. Pharm. Sci, 67(5):523-531 (2005).

Galloway. Dropless Cataract Surgery Offers 'Significant Benefit. Jan. (Year: 2015).

PHARMACEUTICAL OPHTHALMIC COMPOSITIONS

CROSS REFERENCE TO RELATED APPLICATIONS

This is a divisional of U.S. patent application Ser. No. 17/084,514, which was a divisional of U.S. patent application Ser. No. 15/178,812, now abandoned, which was a continuation-in-part patent under 35 U.S.C. § 120 of U.S. patent application Ser. No. 14/227,819, filed Mar. 27, 2014, now abandoned, which in turn claims benefit under 35 U.S.C. § 119(e) to U.S. Provisional Application No. 61/958,170, filed Jul. 22, 2013, the entire contents of each of which being hereby incorporated herein by reference.

FIELD OF THE INVENTION

The present invention relates generally to the field of ophthalmology and more specifically to injectable ophthalmological compositions having anti-bacterial and anti-inflammatory properties, and to methods of preparing such compositions.

BACKGROUND

In ophthalmological treatments and procedures, e.g., cataract surgery, pre- and post-operative eye drops are frequently used by the patients to eliminate or alleviate negative post-surgery complications such as infections, inflammation, and tissue edema. It has been reported that as many as 8% of all ocular surgery patients may suffer from infections, including the potentially catastrophic endophthalmitis, and various negative sight threatening side effects after surgery, such as inflammatory uveitis, corneal edema, and cystoid macular edema.

Typically, the topical postoperative medications are prescribed for at-home use starting before and then after cataract surgery, and are typically self-administered, unless requiring a caregiver or family assistance.

These ophthalmic medication drops include anti-inflammatory and antibiotic agents and are highly effective, but require strict adherence to the treatment regimens, which is often difficult for many patients (with physical limitations or aversions to eyelid touching and manipulation) and is frequently expensive (well over $200 per procedure), causing patients' dissatisfaction. It is desirable to have an alternative procedure that would permit avoiding the necessity of the use of such post-surgery medications to save the associated post-operative trouble and expenses.

One such alternative procedure includes the intraoperative intravitreal injection by an atraumatic transzonular route that can achieve patient outcomes that are as good as, or better than, the current at-home eye drop regimen, removing the issues of compliance and medication administration accuracy. This patent specification discloses pharmaceutical compositions suitable for intraoperative ocular injections that can achieve such positive patient outcomes, and methods of fabricating and administering the same.

SUMMARY

According to one embodiment of the invention, an ophthalmic pharmaceutical composition is provided in a form of suspension, the composition comprising a therapeutic component consisting essentially of a therapeutically effective quantity of an anti-bacterial agent and a therapeutically effective quantity of an anti-inflammatory agent, a combination of at least two pharmaceutically acceptable excipients, and a pharmaceutically acceptable carrier, wherein the composition is suitable for delivery via intraocular injection or via eye drops.

According to another embodiment of the invention, an anti-bacterial agent described herein can be a compound selected from the group of quinolone (including a fluorinated quinolone), e.g., moxifloxacin, and pharmaceutically acceptable salts, hydrates, solvates or N-oxides thereof.

According to yet another embodiment of the invention, an anti-inflammatory agent described herein can be a corticosteroid, e.g., triamcinolone, and pharmaceutically acceptable salts, hydrates, solvates, ethers, esters, acetals and ketals thereof.

According to another embodiment of the invention, the pharmaceutical compositions described herein further include at least two solubilizing and suspending agents of which one is any of non-ionic polyoxyethlene-polyoxypropylene block copolymers, e.g., Poloxamer 407®, and the other is any of water-soluble derivatives of cellulose (e.g., carboxymethyl cellulose, methyl cellulose, hydroxyethyl cellulose, or hydroxypropyl cellulose), non-cross-linked or partially cross-linked polyacrylates, polyoxyethylene sorbitan monolaurates, polyoxyethylene sorbitan monopalmitates, polyoxyethylene sorbitan monostearates, polyoxyethylene sorbitan monooleates or combinations thereof.

According to other embodiments of the invention, the pharmaceutical compositions described herein may be intravitreally transzonularly injected into a mammalian subject as a part of the process of treatment of a variety of ophthalmological diseases, conditions or pathologies associated with intraocular surgery, such as cataracts, retinal and glaucoma disease.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or a biological compound or substance, or a mixture or combination of two or more such compounds or substances, intended for use in the medical diagnosis, cure, treatment, or prevention of disease or pathology.

The term "intraocular injection" refers to an injection that is administered by entering the eyeball of the patient.

The term "transzonular" refers to an injection administered through the ciliary zonule which is a series of fibers connecting the ciliary body and lens of the eye.

The term "intravitreal" refers to an injection administered through an eye of the patient, directly into the inner cavity of the eye.

The term "intraoperative" is defined as an action occurring or carried during, or in the course of, surgery.

The term "suspension" is defined for the purposes of the present application as a two-phase only dispersion system (e.g., a colloidal dispersion) having a first phase and a second phase. It is further specifically provided that dispersion systems having three, four or more phases are not within the meaning of "suspension" for the purposes of the instant application.

Furthermore, the above mentioned first phase of the suspension consists of a multitude of solid particles and is designated and defined as the "dispersed phase", and the above mentioned second phase of the suspension is a liquid and is designated and defined as the "dispersion medium", or, interchangeably and synonymously, the "continuous phase".

Furthermore, the above mentioned dispersed phase is dispersed in the above mentioned dispersion medium, and the term "dispersed" is defined as meaning that the dispersed phase is statistically evenly distributed throughout the entire volume of the suspension, with no statistically meaningful deviations in the concentrations of the dispersed phase in different portions of the suspension.

The terms "anti-bacterial" and "antibiotic" are used herein interchangeably to refer to substances or compounds that destroy bacteria and/or inhibit the growth thereof via any mechanism or route.

The term "anti-inflammatory" refers to substances or compounds that counteract or suppress inflammation via any mechanism or route.

The term "quinolone" for the purposes of this application refers to a genus of anti-bacterial compounds that are derivatives of benzopyridine and in some embodiments include fluorine atom, such as in the following structure ("fluoroquinolone"):

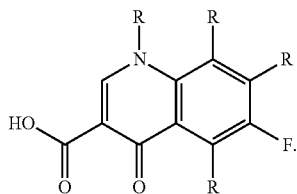

The term "corticosteroid" is defined as a compound belonging to a sub-genus of steroids that are derivatives of corticosterone, the latter having the chemical structure:

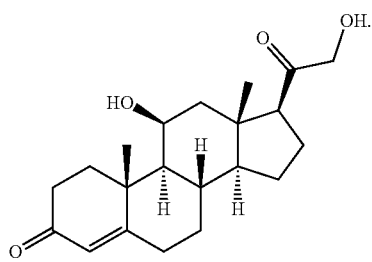

The term "salt" refers to an ionic compound which is a product of the neutralization reaction of an acid and a base.

The terms "solvate" and "hydrate" are used herein to indicate that a compound or a substance is physically or chemically associated with a solvent for "solvates" such as water (for "hydrates").

The term "ether" refers to a chemical compound containing the structure R—O—$R_1$, where two organic fragments R and $R_1$ are connected via oxygen.

The term "ester" refers to a chemical compound containing the ester group R—O—C(Q)-$R_1$, connecting two organic fragments R and $R_1$.

The terms "acetal" and "ketal" refer to a chemical compound containing the functional group R—C($R_1$)O$R_2$)$_2$, where R and $R_2$ are organic fragments and $R_1$ is hydrogen atom (for acetals), and is inclusive of "hemiacetals" where one $R_2$ (but not the other) is hydrogen atom; or where none of R, $R_1$ and $R_2$ is a hydrogen atom and each is an organic fragment (for ketals).

The terms "non-steroid anti-inflammatory drug" or "NSAID" refer to substances or compounds that are free of steroid moieties and provide analgesic, antipyretic and/or anti-inflammatory effects.

The term "carrier" refers to a substance that serves as a vehicle for improving the efficiency of delivery and the effectiveness of a pharmaceutical composition.

The term "excipient" refers to a pharmacologically inactive substance that is formulated in combination with the pharmacologically active ingredient of pharmaceutical composition and is inclusive of bulking agents, fillers, diluents and products used for facilitating drug absorption or solubility or for other pharmacokinetic considerations.

The term "solubilizing agent" for the purposes of the instant application refers broadly to chemical compounds that improve the process of incorporating the solubilizate (i.e., active components described herein) into micelles; in other words the presence of a solubilizing agent makes the process of solubilization faster, easier, and/or more complete as compared with compositions without it.

The term "suspending agent" for the purposes of the instant application refers broadly to chemical compounds that help active pharmaceutical ingredients stay suspended in the formulation and prevents and/or reduces the phase separation of two-phase dispersion systems described herein.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" is defined as a carrier, whether diluent or excipient, that is compatible with the other ingredients of the formulation and not deleterious to the recipient thereof.

The terms "administration of a composition" or "administering a composition" is defined to include an act of providing a compound of the invention or pharmaceutical composition to the subject in need of treatment.

B. Embodiments of the Invention

According to embodiments of the present invention, pharmaceutical compositions intended to prevent and/or treat inflammation and/or infections are provided. The compositions include an active component comprising, consisting essentially of, or consisting of a therapeutically effective quantity of an anti-bacterial agent (i.e., an antibiotic) and a therapeutically effective quantity of an anti-inflammatory agent (e.g., a corticosteroid). In some embodiments, the pharmaceutical compositions can be used for intraocular injections. In other embodiments the pharmaceutical compositions can be used for intra-articular or intra-lesional use. In yet other embodiments the pharmaceutical compositions can be used for delivery via eye drops. The compositions further include one or several pharmaceutically acceptable excipient(s) and one or several pharmaceutically acceptable carrier(s).

The concentration of the anti-bacterial agent in the pharmaceutical composition may be between about 0.01 mg/mL and about 50.0 mg/mL, such as between about 0.5 mg/mL and about 10 mg/mL, for example, about 1.0 mg/mL. The concentration of the anti-inflammatory agent in the pharmaceutical composition may be between about 0.1 mg/mL and about 100.0 mg/mL, such as between about 5.0 mg/mL and about 50.0 mg/mL, for example, about 15.0 mg/mL.

According to further embodiments, the anti-bacterial agent to be employed in the active component of the composition may be selected from the group of quinolones, including fluoroquinolones, and suitable derivatives of the same, such as pharmaceutically acceptable salts, hydrates or solvates thereof. In one embodiment, fluoroquinolone that may be so employed is moxifloxacin (chemically, 1-cyclopropyl-7-[(1S,6S)-2,8-diazabicyclo-[4.3.0]non-8-yl]-6-fluoro-8-methoxy-4-oxo-quinoline-3-carboxylic acid), which is available, e.g., under trade name Avelox® from Bayer Healthcare Corp. of Wayne, N.J., and under other trade names from other suppliers such as Alcon Corp. and Bristol-Myers Squibb Co., and has the following chemical structure:

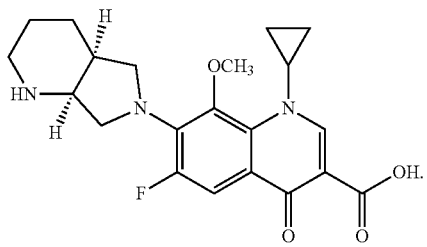 [SMILES: COc1c(N2C[C@@H]3CCCN[C@@H]3C2)c(F)cc2c(=O)c(C(=O)O)cn(C3CC3)c12]

A non-limiting example of a possible alternative fluoroquinolone antibiotic that may be used instead of, or in combination with, moxifloxacin is gatifloxacin. In some further embodiments one or several glycopeptide antibiotic(s), or a combination of some or all of them, may be optionally used as a part of the anti-bacterial agent, in combination with (i.e., in addition to) moxifloxacin. One example of such an acceptable additional glycopeptide antibiotic is vancomycin which can be introduced into the pharmaceutical composition at a concentration between about 1 mg/mL and about 100.0 mg/mL, such as between about 5.0 mg/mL and about 50.0 mg/mL, for example, about 10.0 mg/mL. Vancomycin is available under the trade name Vancocin® from Eli Lilly & Co. of Indianapolis, Ind. Other acceptable additional glycopeptide antibiotics that may be so optionally used include teicoplanin, telavancin, decaplanin, ramoplanin, gentamicin, tobramycin, amikacin, cefuroxime, polymyxin B sulfate, and trimethoprim.

According to further embodiments, the anti-inflammatory agent to be employed in the active component of the composition may be selected from the group of corticosteroids, such as derivatives of corticosterone, and pharmaceutically acceptable salts, hydrates, solvates, ethers, esters, acetals and ketals thereof. For example, a product obtained as a result of a chemically reasonable substitution of any hydrogen and/or hydroxyl group in the molecule of corticosterone may be used. In one embodiment, a corticosteroid that can be so utilized is triamcinolone (chemically, (11β,16α)-9-fluoro-11,16,17,21-tetrahydroxypregna-1,4-diene-3,20-dione) having the following chemical formula:

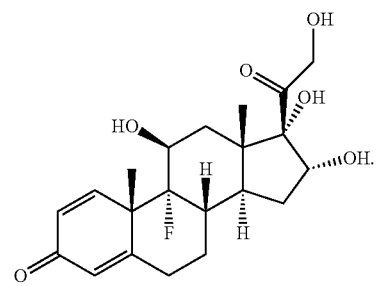

In another embodiment, a corticosteroid that can be so utilized is triamcinolone acetonide (chemically, (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one) which is a ketal derivative of triamcinolone available. e.g., under the trade name Kenalog® from Bristol-Myers Squibb Co. of Princeton, N.J., and under other trade names from other suppliers, and having the following chemical formula:

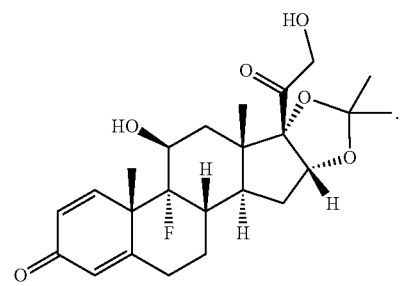

Other corticosteroids, or a combination of some or all of them, may be used instead of all or a portion of triamcinolone and/or of all or a portion of triamcinolone acetonide. Some non-limiting examples of such acceptable other corticosteroids include triamcinolone diacetate, triamcinolone benetonide, triamcinolone furetonide, triamcinolone hexacetonide, betamethasone acetate, dexamethasone, fluorometholone and fluocinolone acetonide.

According to other embodiments, pharmaceutical compositions described herein may further optionally include pharmaceutically effective quantities of one or several non-steroid anti-inflammatory drug(s) or NSAID(s). The concentration of NSAID(s) in the pharmaceutical composition, if used, may be between about 0.1 mg/mL and about 100.0 mg/mL, such as between about 5.0 mg/mL and about 50.0 mg/mL, for example, about 15.0 mg/mL.

If the pharmaceutical compositions disclosed herein do include NSAID(s), it is envisioned that some compositions should be free of the specific NSAID, bromfenac. In other embodiments, however, bromfenac may be used as well as such NSAID(s) as any of ketorolac, etodolac, sulindac, diclofenac, aceclofenac, nepafenac, tolmetin, indomethacin, nabumetone, ketoprofen, dexketoprofen, ibuprofen, flurbiprofen, dexibuprofen, fenoprofen, loxoprofen, oxaprozin, naproxen, aspirin, salicylic acid, diflunisal, salsalate, mefenamic acid, meclofenamic acid, flufenamic acid, tolfenamic acid, meloxicam, piroxicam, ternoxicam, droxicam, lornoxicam, isoxicam, celecoxib, rofecoxib, valdecoxib, parecoxib, lumiracoxib, etoricoxib, firocoxib, nimesulide, clonixin, licofelone, and pharmaceutically acceptable salts, hydrates, solvates, ethers, esters, acetals and ketals thereof.

As mentioned above, the pharmaceutical composition that is the subject matter of the instant application may further optionally include one or several pharmaceutically acceptable excipient(s). Those having ordinary skill in the art will be able to select the suitable excipient(s). It is worth mentioning that when moxifloxacin is used in pharmaceutical formulations, it is often difficult to obtain a stable suspension of another product (e.g., a corticosteroid such as triamcinolone acetonide) that is present in the same formulation and that needs to be in a form of a stable suspension. Without being bound by any particular scientific theory, such difficulties in obtaining the stable suspension are believed to be caused by moxifloxacin's tendency to deactivate many suspending agents resulting in unacceptable coagulation, clumping and flocculation. As a result, normal delivery through a typical 27-29 gage cannula is often difficult or even impossible.

Therefore, it is desirable to select an excipient that is stable in the presence of moxifloxacin and can, therefore, be used as a solubilizing and suspending agent to ensure that the corticosteroid such as triamcinolone acetonide safely forms a stable suspension even when moxifloxacin is also present in the same formulation. Numerous attempts by others to produce a stable moxifloxacin/triamcinolone acetonide pharmaceutical composition suitable for intraocular injection have not been successful.

An excipient that can be used as the solubilizing and stabilizing agent to overcome the above-described difficulties and thus to obtain a stable suspension of the corticosteroid such as triamcinolone acetonide may be a non-ionic polyoxyethlene-polyoxypropylene block copolymer (I) having the following general structure:

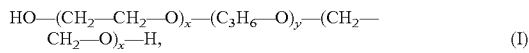
(I)

wherein x is an integer having the value of at least 8 and y is an integer having the value of at least 38.

When a block copolymer (I) is used as the solubilizing and stabilizing agent in the pharmaceutical compositions of the instant invention, its contents in the overall composition may be between about 0.01 mass % and about 10.0 mass % such as between about 1.0 mass % and about 8 mass %, for example, about 5.0 mass %.

One non-limiting example of a specific block copolymer (I) that can be used as the solubilizing and stabilizing agent in the pharmaceutical compositions of the instant invention is the product known under the trade name Poloxamer 407®(poly(ethylene glycol)-block-poly(propylene glycol)-block-poly(ethylene glycol)) available from Sigma-Aldrich Corp. of St. Louis, Mo., with the molecular weight of the polyoxypropylene portion of about 4,000 Daltons, about a 70% polyoxyethylene content, the overall molecular weight of between about 9,840 Daltons and about 14,600 Daltons and having the following chemical structure

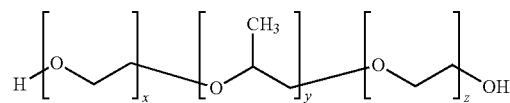

Further presently disclosed embodiments teach that in addition to at least one block copolymer (I) shown above, the presence of which in compositions is required, optionally, a second, a third, etc., solubilizing and suspending agent(s), can be used, if desired, to formulate the excipients to be used in the compositions of the present invention.

In such two-or-more-solubilizing-and-suspending-agents compositions, a block copolymer (I) shown above may be used as the first solubilizing and stabilizing agent in the pharmaceutical compositions of the instant invention, including (poly(ethylene glycol)-block-poly(propylene glycol)-block-poly(ethylene glycol) (i.e., Poloxamer 407®) in the quantities mentioned above.

An excipient that can be used as the second solubilizing and stabilizing agent can be a water-soluble derivative of cellulose, water-soluble, optionally partially cross-linked polyacrylates, and products of Polysorbate family, or combinations thereof.

Suitable water-soluble derivatives of cellulose that may be used include, without limitations, carboxymethyl cellulose, methyl cellulose, hydroxyethyl cellulose, and hydroxypropyl cellulose available, among other sources, from The Dow Chemical Company of Midland, Mich. Examples of acceptable water-soluble, partially cross-linked, polyacrylates that may be used include, without limitations, such as polymers of the Carbopol® family available from The Lubrizol Corporation of Wickliffe, Ohio. Typically, the cross-linking agents that may be used to cross-link such polyacrylates are allyl sucrose or allyl pentaerythritol.

Suitable products of Polysorbate family (i.e., ethoxylated sorbitan esterified with fatty acids) that may be used include, without limitations, polyoxyethylene sorbitan monolaurates, polyoxyethylene sorbitan monopalmitates, polyoxyethylene sorbitan monostearates, or polyoxyethylene sorbitan monooleates, some of which are also known as Tween® products, such as Polysorbate 80®) can be used as the second solubilizing and stabilizing agent. Such products are available from Croda Americas, L.L.C. of Wilmington, Del. or from Sigma-Aldrich Corp., among other suppliers making these products available.

One typical product of the latter family that can be used is Polysorbate 80® (chemically, polyoxyethylene (20) sorbitan monooleate, also known as sorbitan mono-9-octadecenoate poly(oxy-1,2-ethanediyl), i.e., a product of polycondensation of polyethoxylated sorbitan and oleic acid having 20 units derived from ethylene glycol), a nonionic surfactant and emulsifier having the structure:

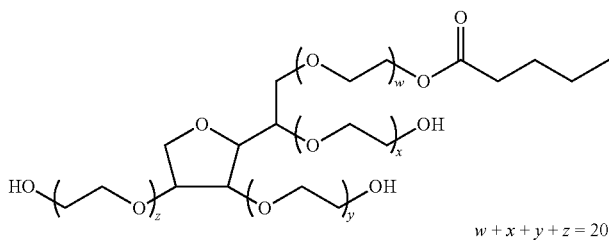
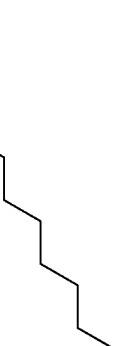

$w + x + y + z = 20$

Non-limiting examples of some other excipients and carriers that may be used in preparing in the pharmaceutical compositions of the instant invention include edetate calcium disodium (EDTA, a chelating agent), hydrochloric acid (the pH adjuster) and sterile water.

According to embodiments of the present application, the pharmaceutical compositions described herein are formulated as stable two-phase suspensions as defined above. More specifically, according to these embodiments, the suspensions at issue consist of two phases, i.e., the dispersed phase that is dispersed within the dispersion medium. The dispersed phase consists of solid particles consisting of a therapeutically effective quantity of a corticosteroid. No compounds other that corticosteroids described hereinabove are present within the solid particles that form the dispersed phase.

According to such embodiments, the dispersion medium is a liquid that includes all other compounds that are present in the pharmaceutical compositions described in the application. The application envisions no embodiment where corticosteroid can be used outside the dispersed phase such as in the dispersion medium. Specifically, the dispersion medium may include the following components (a)-(e):
 (a) at least one anti-bacterial agent of the quinolone group (i.e., quinolone, a fluorinated quinolone and derivatives as described);
 (b) at least two solubilizing and suspending agents (i.e., a non-ionic polyoxyethylene-polyoxypropylene block copolymer plus a polysorbate);
 (c) optionally, at least one glycopeptide antibiotic (i.e., vancomycin, or other antibiotic(s) described hereinabove);
 (d) also optionally, at least one non-steroid anti-inflammatory drug such as bromfenac or other NSAIDs described hereinabove; and
 (e) a carrier.

According to further embodiments, methods for fabricating the above-described pharmaceutical compositions are provided. A one-batch formulation method may be used, where the components of the pharmaceutical formulation can be combined in single container; the components may be added to the container simultaneously or consecutively.

In one exemplary, non-limiting procedure, the process of preparing the pharmaceutical compositions described hereinabove may commence by forming the aqueous dispersion medium.

To form the aqueous dispersion medium, a quantity of an anti-bacterial agent such as moxifloxacin may be put into a mixing container followed by adding a quantity of sterile water and hydrochloric acid to obtain a slightly acidic mixture (e.g., having pH of about 6.5) which can be stirred until a clear solution is obtained. In case of moxifloxacin/HCl system, the solution is stable, allowing the formulation to remain closed system thus preventing contamination and the loss of sterility.

After such clear stable solution has been formed, more components could be added to the solution that is to become the dispersion medium of the final suspension, i.e., a quantity of Poloxamer 407® and/or a quantity of polysorbate 80, a quantity of edetate calcium disodium, optionally a quantity of an antibiotic (e.g., vancomycin) and optionally a quantity of an NSAID (e.g., bromfenac) may be all added to the same container with the already prepared moxifloxacin/HCl solution.

At the same time, a quantity of corticosteroid such as micronized triamcinolone acetonide can be added to the above described solution, followed by stirring everything together (e.g., by spinning) for a period of time, e.g., about 6 hours, until a homogenous suspension has been obtained. In that suspension two phases can be formed: the dispersed phase of the corticosteroid and the dispersion medium into which the aqueous solution described above has now been transformed.

The resulting suspension may then be transferred into single dose vials, capped, sealed, autoclaved and shaken until cool. Finally, a complete testing for sterility and the presence of endotoxin may be performed on the product according to commonly used methods known to those having ordinary skill in the art.

Pharmaceutical compositions prepared as described above can be used to prevent complications that may arise after ophthalmic surgical operations and procedure. For example, the formulations can be used during any intraocular surgery, such as cataract surgery, planned vitrectomy or glaucoma procedures, to prevent or at least substantially reduce the risk of post-surgery complications, such as the development of endophthalmitis or cystoid macular edema (CME), without having the patient use pre- or post-operative topical ophthalmic drops. Individuals with evidence of endophthalmitis from prior surgical procedures or traumatic ocular penetration will benefit from concurrent injection of these formulations to sterilize infection and reduce damaging inflammation.

Pharmaceutical formulations described herein can be delivered via intraocular intravitreal injection which can be transzonular, or, if desired not transzonular. Intraocular intravitreal injection of this formulation, whether done via transzonular or via direct pars plana (trans-scleral) injection, delivers potent broad spectrum antibiotics directly into the suppurative tissue without requiring the urgent compounding of multiple individual medications or multiple individual injections into the eye.

Typically, a pharmaceutical composition described above will be intraocularly administered to a mammalian subject (e.g., humans, cats, dogs, other pets, domestic, wild or farm animals) in need of emergent, urgent or planned ophthalmic surgery treatment. The effect achieved by such use of pharmaceutical composition described above may last up to four weeks. The composition is to be injected intravitreally and trans-zonularly using methods and techniques known to those having ordinary skilled in the art of ophthalmology. In some embodiments, the injection can be intraoperative.

The delivery through a typical 27 gauge cannula can be employed utilizing a 1 mL TB syringe, with attention to re-suspending the formulation using momentary flicks and shake just prior to injection. The medicinal volume (i.e., dosage) required of this formulation varies based on the type of intraocular procedure, the degree of postoperative inflammation induced or anticipated, the risk assessment for postoperative infection, and anatomic considerations regarding the available volume for the injection being added to a closed intraocular space.

It is worth mentioning that while intracameral (that is, anterior chamber) injections are within the scope of the instant invention such injections instead of posterior chamber (intravitreal) injection may not be satisfactory in some cases, as the suspension clogs the trabecular meshwork and aggravates intraocular drainage, resulting in an intraocular pressure rise postoperative. This is avoided with intravitreal injection, in addition to retaining the formulation components into the protein matrix of the vitreous of a greater duration. Anterior chamber wash out occurs over hours (antibiotic in solution) and days (steroid in suspension), while intravitreal injection is retained for weeks.

In alternative embodiments, if desired or necessary the formulations may also be delivered in the form of eye drops or eye sprays, as well as via subconjunctival injection, intraocular intracameral injection, sub-tenon injection, intra-articular injection or intra-lesional injection, particularly, in, but not limited to, some cases when necessary to deliver additional medication when local ocular inflammation and extra-ocular infection need suppression. Intravitreal delivery of steroid has historically been used to treat clinically significant cystoid macular edema (CME); the application of this formulation into the vitreous during routine intraocular procedures brings more aggressive prophylaxis against CME occurrence. Additionally, the suspension of this formulation is useful for staining vitreous during planned and unplanned vitrectomies, improving visualization of this otherwise transparent intraocular tissue, improving vitrectomy outcomes and reducing complications resulting from inadequate or tractional vitreous removal. In still further embodiments, there is also envisioned intra-canalicular delivery, i.e., delivery via a lacrimal canaliculus implant.

In some further alternative embodiments, instead of delivering the above-described compositions comprising both anti-bacterial and anti-inflammatory agents, consecutive injections may be used instead, if desired. For example, triamcinolone may be injected first, immediately followed by the injection of moxifloxacin or vice versa.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular ophthalmological condition being treated.

In additional embodiments, pharmaceutical kits are provided. The kit includes a sealed container approved for the storage of pharmaceutical compositions, the container containing one of the above-described pharmaceutical compositions. An instruction for the use of the composition and the information about the composition are to be included in the kit.

The following examples are provided to further elucidate the advantages and features of the present invention, but are not intended to limit the scope of the invention. The examples are for the illustrative purposes only. USP pharmaceutical grade products were used in preparing the formulations described below.

C. Examples

Example 1. Preparing a Pharmaceutical Composition

A pharmaceutical composition was prepared as described below. The following products were used in the amounts and concentrations specified:
(a) about 1.5 g of triamcinolone acetonide, at a concentration of about 15.0 mg/mL;
(b) about 0.1 g of moxifloxacin hydrochloride, at a concentration of about 1.0 mg/mL;
(c) about 1 mL of polysorbate 80, at a concentration of about 10 mass %;
(d) about 0.2 g of edetate calcium disodium, at a concentration of about 0.2 mass %;
(e) about 1 g of Poloxamer 407*, at a concentration of about 1.0 mass %;
(f) hydrochloric acid, to adjust pH to about 6.5; and
(g) about 100.0 mL of sterile water for injection.

Moxifloxacin hydrochloride was placed into a de-pyrogenated beaker with a spin bar. Sterile water for injection was added to about ⅓ of the volume of the beaker. While spinning, moxifloxacin was dissolved by adding hydrochloric acid until a clear solution having the final pH of about 6.5 was obtained.

The solution was combined with micronized triamcinolone acetonide, Poloxamer 407*, edetate calcium disodium and polysorbate 80 and allowed to spin for about 6 hours until a hydrated and homogenous suspension was obtained.

The suspension was transferred into de-pyrogenated, single dose vials (2 mL size), capped and sealed, followed by autoclaving and shaking the vials until cool. Complete sterility and endotoxin testing was performed by an outside laboratory to ensure safety.

The formulation prepared as described above was tested for stability after 6 months of storage. After this period of storage no loss of potency was observed (as measured by HPLC); the formulation was visually stable at room temperature and readily re-suspended with gentle shaking with no increase of particle size or flocculation.

Example 2. Preparing a Pharmaceutical Composition Containing Vancomycin

A pharmaceutical composition was prepared as described in Example 1, supra. The composition was autoclaved and sonicated for about 60 minutes and about 96 mL of the composition were combined with about 4 mL of vancomycin at a concentration of about 250 mg/mL. The pH of the mixture was adjusted to about 6.0-6.5 using hydrochloric acid. The product was then transferred into vials (at about 1 mL plus 5 drops per vial) and frozen. The product has kept its stability and potency for at least six months.

Example 3. Using a Pharmaceutical Composition

A pharmaceutical composition fabricated as described in Example 1, supra, was administered to about 1,600 patients. To each, it was introduced using intravitreal transzonular injection. The injection was intraoperative. Only a very few patients, at the rate of about only 1 in 4,000, have developed any infection or suffered from other side effects that required further treatment, which is a substantial improvement over a typical rate of about 8% for the patients that did not receive the injection.

Example 4. Preparing a Pharmaceutical Composition Containing NSAID Bromfenac

A pharmaceutical composition may be prepared as described below. The following products may be used in the amounts specified:
(a) about 10.0 g of triamcinolone acetonide;
(b) about 5.454 g of moxifloxacin hydrochloride monohydrate;
(c) about 1.035 g of bromfenac sodium powder;
(d) about 10.0 mL of an aqueous solution of polysorbate 80, at a concentration of about 1.0 mass %;
(e) about 4.0 g of boric acid powder;
(f) about 14.0 g of Poloxamer 407®;
(g) about 3.17 g of sodium chloride granules;
(h) 20% solution of sodium hydroxide, to adjust pH; and
(i) about 1.0 L of sterile water for injection.

Moxifloxacin hydrochloride may be placed into a de-pyrogenated beaker with a spin bar. Sterile water for injection may be added, about 60% of the total volume of water. While spinning, moxifloxacin may be dissolved by adding sodium hydroxide to adjust the pH to about 7.4 to 7.8, followed by additional stirring for about 5 minutes, until a clear solution is obtained. Bromfenac may then be added, with continued stirring, until completely dissolved which will be indicated by the solution being visibly clear. The pH then may be then adjusted again to be maintained it in the range of 7.4 to 7.8.

The solution may be combined with polysorbate 80, Poloxamer 407 and boric acid, with continued stirring, followed by slowly adding triamcinolone acetonide, the remainder of water, with continued spinning for about 20 minutes, until a hydrated and homogenous product is obtained.

The product may then be transferred into pre-sterilized de-pyrogenated, 100 mL vials, capped and sealed, followed by autoclaving (about 121° C. and about 15.0 psi of pressure for about 30 minutes) and shaking and sonicating the vials for about 30 minutes.

Although the invention has been described with reference to the above examples, it will be understood that modifications and variations are encompassed within the spirit and scope of the invention. Accordingly, the invention is limited only by the following claims.

What is claimed is:

1. A pharmaceutical composition, comprising:
(a) a therapeutically effective quantity of triamcinolone or a derivative thereof;
(b) a therapeutically effective quantity of moxifloxacin;
(c) a non-ionic poly(ethylene glycol)-block-poly(propylene glycol)-block-poly(ethylene glycol) block copolymer having a molecular weight of the polyoxypropylene portion of about 4,000 Daltons and about a 70% polyoxyethylene content, with an overall molecular weight of between about 9,840 Daltons and about 14,600 Daltons, wherein the concentration of the non-ionic poly(ethylene glycol)-block-poly(propylene glycol)-block-poly(ethylene glycol) block copolymer is between about 1 mass % and about 2 mass % of the pharmaceutical composition;
(d) about 1% of polysorbate 80; and
(e) a pharmaceutically acceptable carrier.

2. The composition of claim 1, wherein said composition further comprises a therapeutically effective quantity of a glycopeptide antibiotic selected from the group consisting of vancomycin, teicoplanin, telavancin, decaplanin, ramoplanin, gentamicin, tobramycin, amikacin, cefuroxime, polymyxin B sulfate, trimethoprim, and a combination thereof.

3. The composition of claim 2, wherein said antibiotic is vancomycin.

4. The composition of claim 1, wherein said pharmaceutically acceptable carrier is selected from the group consisting of sterile water, a sterile water solution of edetate calcium disodium, a sterile water solution of hydrochloric acid, and combinations thereof.

* * * * *